United States Patent
Götzmann et al.

(10) Patent No.: US 6,512,133 B1
(45) Date of Patent: Jan. 28, 2003

(54) PROCESS FOR THE PRODUCTION OF PHOSPHORIC ACID ESTERS OR PHOSPHORIC ACID ESTER MIXTURES OF POLYHYDRIC ALCOHOLS AND USE THEREOF

(75) Inventors: Karl Götzmann, Budenheim (DE); Hans-Dieter Nägerl, Dudenhofen (DE); Klaus Sommer, Bad Durkheim (DE)

(73) Assignee: Chemische Fabrik Budenheim Rudolf, Budenheim (DE)

( * ) Notice: Subject to any disclaimer, the term of this patent is extended or adjusted under 35 U.S.C. 154(b) by 38 days.

(21) Appl. No.: 09/696,595

(22) Filed: Oct. 25, 2000

(30) Foreign Application Priority Data

Oct. 26, 1999 (DE) .......................................... 199 51 385

(51) Int. Cl.⁷ .................................................. C07F 9/09
(52) U.S. Cl. ...................................................... 558/114
(58) Field of Search ............................. 558/70, 87, 89, 558/113, 114

(56) References Cited

U.S. PATENT DOCUMENTS

| | | | |
|---|---|---|---|
| 2,656,372 A | * 10/1953 | Ernst et al. ................. | 260/461 |
| 3,331,896 A | * 7/1967 | Eiseman, Jr. et al. ....... | 260/980 |
| 3,584,087 A | * 6/1971 | Mausner et al. ............. | 260/980 |
| 4,153,649 A | * 5/1979 | Griffin ........................ | 260/950 |

\* cited by examiner

*Primary Examiner*—Joseph K. McKane
*Assistant Examiner*—Golam M M Shameem
(74) *Attorney, Agent, or Firm*—Killworth, Gottman, Hagan & Schaeff, L.L.P.

(57) ABSTRACT

A process for the production of phosphoric acid esters or phosphoric acid ester mixtures of polyhydric alcohols by reaction of the polyhydric alcohols with phosphorus pentoxide is characterized in that the amount of phosphorus pentoxide which is required for the esterification operation is suspended in an amount of the ester or ester mixture to be produced, thereupon the amount of polyhydric alcohol required for the esterification operation and possibly water is added at a temperature in the range of between 20 and 180° C., thereupon the esterification reaction is substantially completely executed and thereafter the product is obtained. The products of the process are used for the production of flame-proofing treatments.

8 Claims, No Drawings

PROCESS FOR THE PRODUCTION OF PHOSPHORIC ACID ESTERS OR PHOSPHORIC ACID ESTER MIXTURES OF POLYHYDRIC ALCOHOLS AND USE THEREOF

For example WO 93/05 118 discloses the intumescent properties of compositions which contain phosphoric acid esters of polyhydric alcohols. Such phosphoric acid esters are used in many different ways in industry, in particular in the sector concerning flame-proofing of plastic materials. Those phosphoric acid esters are halogen-free and are therefore particularly well suited for use as flame-proofing agents.

It is also already known, such as for example from Houben Weyl 12/2, pages 156 ff and 226 ff, for phosphoric acid esters of that kind to be produced by alcoholysis from phosphorus pentoxide and/or polyphosphoric acid and the desired polyhydric alcohols or mixtures thereof. The direct reaction of alcohols with phosphorus pentoxide however gives rise to major problems as phosphorus pentoxide is extremely reactive and therefore easily gives rise to dehydration phenomena and thus decomposition of the organic components with decoloration as far as carbon formation. In order to prevent this WO 93/05 118, instead of phosphorus pentoxide, uses mixtures of polyphosphoric acid with phosphorus pentoxide, in which respect however only a maximum of 50% of the amount of phosphorus can be introduced in the form of phosphorus pentoxide. Another possible way of reducing the reactivity of phosphorus pentoxide is described in DE-A-3 502 705 by means of a given temperature-control procedure. Japanese patent publications Nos. 04 210 221, 56 092 294 and 49 055 669 follow yet a different path insofar as they dilute the reaction mixture with tetrahydrofuran, hydrocarbons such as n-hexane, or chloroform. U.S. Pat. No. 4,153,649, DE-A-2 941 419 and DE 3 520 053 operate with excessive alcohols.

All those processes suffer from the disadvantage that subsequent to the esterification they require special purification and cleaning operations.

SUMMARY OF THE INVENTION

Therefore the basic object of the invention is to obtain phosphoric acid esters or mixtures of polyhydric alcohols without decomposition reactions and without the need for subsequent purification operations and to be able to use them in the form as they are removed from the reaction container, for the production of flame-proofing finishes.

The process according to the invention for the production of phosphoric acid esters or phosphoric acid ester mixtures of polyhydric alcohols by reaction of the polyhydric alcohols with phosphorus pentoxide is characterised in that the amount of phosphorus pentoxide which is required for the esterification operation is suspended in an amount of the ester or ester mixture to be produced, thereupon the amount of polyhydric alcohol required for the esterification operation and possibly water is added at a temperature in the range of between 20 and 180° C., thereupon the esterification reaction is substantially completely executed and then the product is obtained.

That process can entail operating with stoichiometric or substantially stoichiometric amounts of phosphorus pentoxide, polyhydric alcohol and possibly water, so that practically only the desired ester or esters is or are produced and no subsequent separation of excess starting substances or solvents has to be effected.

The addition of polyhydric alcohol and optionally water is advantageously effected at a temperature in the range of between 20 and 150° C., and subsequent completion of the esterification reaction is desirably implemented for a period of between 1 and 6 hours at at least the temperature of the addition of polyhydric alcohol. Desirably, in completing the esterification reaction, heating and agitation are effected until a clear fluid has occurred, which shows that the reaction was completely implemented.

When the reaction is concluded the freshly produced amount of phosphoric acid ester or phosphoric acid ester mixture is removed from the reaction container. Thereupon the residual amount of phosphoric acid ester or mixture which has remained in the reaction container can be used to begin a fresh start for the reaction by phosphorus pentoxide being freshly added and suspended in the finished ester or ester mixture.

In particular for further use for the production of flame-proofing finishes, it is desirable to add small amounts of boric acid to the reaction mixture. The additional amount of boric acid is preferably between 0.2 and 6% by weight, preferably being about 3% by weight with respect to the total amount of added phosphorus pentoxide, polyhydric alcohol and optionally water. In a fire situation, in particular in relation to flame-proofing finishes for cellulose materials, the boron component in the esters or ester mixtures produced in accordance with the invention prevents the fire from continuing to glow afterwards and suppresses the formation of fumes.

DETAILED DESCRIPTION OF THE PREFERRED EMBODIMENT

The polyhydric alcohols used for the process according to the invention are for example and desirably ethane-1,2-diol, propane-1,2- and 1,3-diol, butane-1,2-, -1,3-, -1,4- and -2,3-diol, glycerine, trimethylolmethane, -ethane and -propane, neopentylglycol, erythritols, pentaerythritol, di- and polypentaerythritols, pentitols such as arabitol and xylitol, hexitols such as mannitol and sorbitol innositols, dihydroxybenzols and 2,3-dimethylol-1,3-dihydroxybenzol as well as mixtures thereof.

In many cases the combinations of the phosphoric acid esters or ester mixtures produced in accordance with the invention, with polyvinyl amine or polyethylene imine, are found to be advantageous in particular for further use for the production of flame-proofing finishes. Melamine and guanidine salts of the phosphoric acid esters are found to be suitable, in combination with the phosphoric acid esters produced in accordance with the invention. Those additives are thermally stable and can therefore be incorporated into melted-on plastic materials. Methylol melamines and the precondensates thereof can also be combined with the phosphoric acid esters produced in accordance with the invention and used to produce flame-inhibiting treatments.

For example phenol, melamine or urea formaldehyde resins, polyacrylate or polyvinyl acetate dispersions or epoxy resins are suitable as binding agents for the flame-proofing treatment.

Preferably the phosphoric acid esters or mixtures produced in accordance with the invention are used for the production of a flame-proofing treatment of or finish on laminate composite materials.

Laminate composite materials are used in many sectors as in the packaging sector, in the domestic, sporting, technological and building areas but also in aircraft, automobile and apparatus engineering, in cooling technology and in relation to highly stressed machine parts. The large number of possible forms and number of conceivable combinations of starting materials afford a wide spectrum in terms of areas of use. Primarily wood, metals, glass as well as inorganic and organic polymers fall to be considered as constituents of such laminate composite materials. The laminate composite systems also include laminates of the most widely varying kinds, moulded laminate material, corrugated cardboard or fibreboard, packaging crepe, thermal wallpapers, roof insulations, non-woven fabric combinations involving the most widely varying kinds of stabilisation, sandwich components, lined or coated textiles, cable sheathings and many others.

The binding agents used for fixing the phosphoric acid esters and mixtures produced in accordance with the invention can also be used at the same time as binding agents for the lamination of various materials. For the production of laminates the carrier or backing materials can be impregnated by dipping or lacquering or coating and hardened for example at temperatures of between 100 and 200° C. in presses.

When using the phosphoric acid esters or mixtures produced in accordance with the invention for flame-proofing treatments desirably between 10 and 40% of the phosphoric acid esters or mixtures is added to the binding agent system. The additional amounts of binding agent can be reduced by pre-impregnation of the carrier material. Optimum flame-proofing is achieved if both the carrier material and also the cover layers of the composite material contain the phosphoric acid esters or mixtures thereof which are produced in accordance with the invention.

Non-woven fabrics comprising inorganic or organic fibres or mixtures thereof are desirably sprayed prior to stabilisation thereof with solutions of the phosphoric acid esters or phosphoric acid ester mixtures or with mixtures of binding agent resin and phosphoric acid ester, laid and stabilised.

The flame-proofing compositions produced from the phosphoric acid esters and mixtures which are produced in accordance with the invention afford the advantages that the flammability of the composite systems is reduced, flame formation and development is inhibited, flame propagation and spread is restricted, the predetermined structures, their integrity and function are maintained in the fire situation, a protective layer is produced which protects articles or components disposed therebeneath from the effect of flame and the development of combustible gases is prevented and in a fire situation no additional gases are produced from the composition.

In order that the invention may be more readily understood, reference is made to the following examples, which are intended to be illustrative of the invention but are not intended to be limiting in scope.

EXAMPLE 1

500 g of ethylene glycol diphosphoric acid monoester is placed in a round-bottom flask with a useful content of 1 liter, which is provided with an agitator, a thermometer, a reflux condenser and a dropping funnel. 142 g of phosphorus pentoxide is introduced therein with agitation at ambient temperature and suspended. A mixture comprising 52 g of ethylene glycol and 18 g of water can then be slowly added by dropping, with the temperature in the reaction vessel being maintained below 60° C. When the prescribed amount of ethylene glycol/water mixture is added, the temperature is raised to between 120 and 130° C. and agitation is effected at that temperature until a clear fluid is produced. After the mixture has been cooled to ambient temperature the increase in mass in terms of ethylene glycol diphosphoric acid monoester (222 g) is removed before the next reaction is begun.

EXAMPLE 2

500 g of pentaerythritol tetraphosphoric acid monoester is disposed in the same apparatus as described in Example 1. Because of the viscosity of that substance, it is firstly heated with agitation to a temperature of between 80 and 90° C. When that temperature is reached 142 g of phosphorus pentoxide is added and suspended with agitation. A pasty mixture comprising 68 g of pentaerythritol and 18 g of water is then added in a portion-wise manner. When everything has been added, the temperature is raised to 150° C. and agitation is effected at that temperature until a clear fluid is produced. After cooling to about 80° C. the resulting amount of pentaerythritol tetraphosphoric acid monoester (228 g) is removed. A fresh reaction can thereafter be begun.

EXAMPLE 3

An installation comprising a steam-heated vessel of a capacity of 350 l, of high-quality steel, which is equipped with an agitator, is filled with 220 kg of phosphoric acid partially mixed ester. The mixed ester involved is heated to between 80 and 90° C. and then 105 kg of phosphorus pentoxide is added and suspended in the mixed ester. A suspension of 78 kg of pentaerythritol in 47 kg of ethylene glycol is then slowly added to the ester/phosphorus pentoxide mixture. In that operation the temperature rises to between about 105 and 110° C. After everything has been added the temperature is raised to 130° C. After an agitation time of 3 hours, a clear fluid has been formed. The mass is now cooled to about 80° C. and the increase of mass of 230 kg of phosphoric acid partially mixed ester is removed. The mixed ester removed comprises primary and secondary esters of orthophosphoric acid. A fresh esterification operation can then be begun.

EXAMPLE 4

A carrier material comprising a plurality of layers of paper and two cover sheets of glass fibre cloth is impregnated with a 1:1-mixture comprising a 30% melamine resin solution and a 70% phosphoric acid ester solution, produced from phosphorus pentoxide, glycol and pentaerythritol in accordance with Example 3 and pressed out by way of a squeeze roller in such a way that there is a dressing coating of around 130%. The material is dried in a circulating air drying cabinet at 40° C. Hardening is then effected in a heating press at 140° C. and at between 40 and 60 bars. The pressed laminate material obtained in that way satisfies the VO-conditions in the combustion test in accordance with UL94.

EXAMPLE 5

A honeycomb panel of Nomex paper is dipped into a mixture comprising a 25% solution of a melamine resin with a 75% phosphoric acid ester solution (mixing ration of 5:2), and excess resin solution is removed by centrifuging so that a finishing coating of around 100% remains behind. Drying is then effected followed by hardening for 30 minutes at between 100 and 120° C. The patterns satisfy the requirements of the OSU-test in regard to heat development and the conditions of the Mil-STD 401 B-test.

EXAMPLE 6

A loose mixed non-woven fabric of cellulose and acrylonitrile fibres, which is between 5 and 10 mm in thickness, is sprayed with a 1:1 mixture comprising a urea solution and a phosphoric acid ester solution (40% in each case), produced from phosphorus pentoxide, neopentyl glycol and pentaerythritol in a mixing ratio of 1:2.0:0.75 so as to involve a degree of absorption of around 80%. The material is laid upon itself five times and hardened in a heating press at 145° C. and 5 bars for 20 minutes.

EXAMPLE 7

A 30 mm thick PMI-foam plate is impregnated with a mixture comprising respectively a 25% solution of a melamine pre-condensate and a phosphoric acid ester consisting of phosphorus pentoxide, pentaerythritol and trimethylol propane with a content of 2% boric acid, wherein after dripping off the degree of bath absorption is 135%. The dried foam plate is covered on both sides with a laminate from Example 4 and hardened in a heating plate at 160° C. It satisfies the conditions of the edge flaming test.

While representative embodiments and certain details have been shown for purposes of illustrating the invention, it will be apparent to those skilled in the art that various changes in the methods and apparatus disclosed herein may be made without departing from the scope of the invention, which is defined in the appended claims.

What is claimed is:

1. A process for the production of a phosphoric acid ester or a mixture of phosphoric acid esters comprising:
   a) suspending phosphorous pentoxide in a phosphoric acid ester or phosphoric acid ester mixture to be produced;
   b) adding to the phosphorous pentoxide suspension a reactant selected from the group consisting of a polyhydric alcohol and a polyhydric alcohol and water at a temperature of between 20 and 180° C. such that a reaction is initiated between the phosphorous pentoxide and the polyhydric alcohol to produce the phosphoric acid ester or phosphoric acid ester mixture.

2. A process for the production of a phosphoric acid ester or a mixture of phosphoric acid esters comprising:
   a) suspending phosphorus pentoxide in a solution of a phosphoric acid ester or mixture of phosphoric acid esters to be produced,
   b) adding a polyhydric alcohol to the solution, and
   c) reacting the phosphorus pentoxide and polyhydric alcohol; wherein the phosphoric acid ester or mixture of phosphoric acid esters produced do not require subsequent purification prior to use.

3. The process of claim 2 wherein water is added to said solution with said polyhydric alcohol.

4. The process of claim 3 wherein substantially stoichiometric amounts of phosphorus pentoxide, polyhydric alcohol and water are added.

5. The process of 3 wherein said polyhydric alcohol and water are added at a temperature of between 20 and 150° C.

6. The process of claim 3 wherein the reaction is completed within 1 to 6 hours at at least the temperature of addition of said polyhydric alcohol and water.

7. The process of claim 3 wherein an amount of between 0.2 and 6% by weight of boric acid is added based on the total amount of phosphorous pentoxide, polyhydric alcohol and water.

8. A process according to claim 2 herein the polyhydric alcohol is selected from the group consisting of ethane-1,2-diol, propane-1,2- and -1,3-diol, butane-1,2-, -1,3-, -1,4- and -2,3-diol, glycerine, trimethylolmethane, -ethane and -propane, neopentylglycol, erythritols, pentaerythritol, di- and polypentaerythritols, pentitols, hexitols, innositols, dihydroxybenzols, 2,3-dimethylol-1,3-dihydroxybenzol, or mixtures thereof.

* * * * *

UNITED STATES PATENT AND TRADEMARK OFFICE
CERTIFICATE OF CORRECTION

PATENT NO. : 6,512,133 B1
DATED : January 28, 2003
INVENTOR(S) : Karl Götzmann et al.

It is certified that error appears in the above-identified patent and that said Letters Patent is hereby corrected as shown below:

<u>Column 6,</u>
Line 27, "claim 2 herein" should be -- claim 2 wherein --.

Signed and Sealed this

Ninth Day of September, 2003

JAMES E. ROGAN
*Director of the United States Patent and Trademark Office*

UNITED STATES PATENT AND TRADEMARK OFFICE
CERTIFICATE OF CORRECTION

PATENT NO.     : 6,512,133 B1                                              Page 1 of 1
DATED          : January 28, 2003
INVENTOR(S)    : Karl Götzmann et al.

It is certified that error appears in the above-identified patent and that said Letters Patent is hereby corrected as shown below:

<u>Title page,</u>
Item [73], Assignee, "Chemische Fabrik Budenheim Rudolf, Budenheim (DE)" should be -- Chemische Fabrik Budenheim Rudolf A. Oetker, Budenheim (DE) --.

Signed and Sealed this

Fourth Day of November, 2003

JAMES E. ROGAN
*Director of the United States Patent and Trademark Office*